United States Patent [19]

Knops et al.

[11] 4,267,186

[45] May 12, 1981

[54] COMBATING FUNGI WITH SUBSTITUTED SPIRO-DERIVATIVES OF 3-(3,5-DIHALOGENOPHENYL)-OXAZOLI-DINE-2,4-DIONES (THIONE-ONES)

[75] Inventors: Hans-Joachim Knops, Wuppertal; Hans-Georg Heine, Krefeld; Wilfried Draber, Wuppertal; Wilhelm Brandes, Leichlingen, all of Fed. Rep. of Germany

[73] Assignee: Bayer Aktiengesellschaft, Leverkusen, Fed. Rep. of Germany

[21] Appl. No.: 95,715

[22] Filed: Nov. 19, 1979

[30] Foreign Application Priority Data

Dec. 7, 1978 [DE] Fed. Rep. of Germany ....... 2852924

[51] Int. Cl.³ .................... A01N 43/76; C07D 261/04
[52] U.S. Cl. ..................................... 424/272; 548/216
[58] Field of Search .......................... 548/216; 424/272

[56] References Cited

U.S. PATENT DOCUMENTS

| | | | |
|---|---|---|---|
| 3,311,655 | 3/1967 | Boileau et al. | 548/216 |
| 3,586,697 | 6/1971 | Ozaki et al. | 260/326.5 FM |
| 3,741,981 | 6/1973 | Fujinami et al. | 260/326.5 FM |
| 3,745,170 | 7/1973 | Fujinami et al. | 260/326.5 FM |

OTHER PUBLICATIONS

Fujinami et al., "Agr. Biol. Chem.", vol. 35, No. 11, pp. 1707–1719 (1971).

Primary Examiner—Anton H. Sutto
Attorney, Agent, or Firm—Sprung, Felfe, Horn, Lynch & Kramer

[57] ABSTRACT

Substituted spiro-derivatives of 3-(3,5-dihalogenophenyl)-oxazolidine-2,4-diones(thione-ones) of the formula

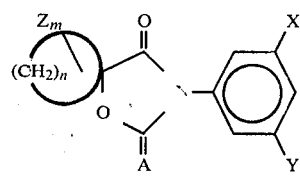

in which
A is oxygen or sulphur,
X and Y each independently is halogen,
Z each independently is alkyl or a fused cycloalkane or cycloalkene ring,
m is 1, 2, 3 or 4, and
n is 2 or 3.

which possess fungicidal properties.

10 Claims, No Drawings

COMBATING FUNGI WITH SUBSTITUTED SPIRO-DERIVATIVES OF 3-(3,5-DIHALOGENOPHENYL)-OXAZOLIDINE-2,4-DIONES (THIONE-ONES)

The present invention relates to and has for its objects the provision of particular new substituted spiro-derivatives of 3-(3,5-dihalogenophenyl)-oxazolidine-2,4-diones (thione-ones) which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed that certain thiuram-disulphides, for example tetramethyl-thiuram-disulphide, exhibit good fungicidal properties (see U.S. Pat. No. 1,972,961). The action of this category of substances, in certain areas of indication, is however not always fully satisfactory, especially if small amounts and low concentrations are used.

The present invention now provides, as new compounds, the substituted spiro-derivatives of 3-(3,5-dihalogenophenyl)-oxazolidine-2,4-diones(thione-ones) of the general formula

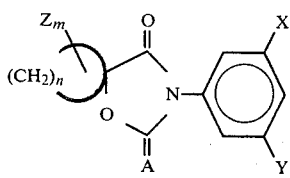

in which
A represents oxygen or sulphur,
X and Y are identical or different and each represent halogen,
Z represents alkyl or a fused cycloalkane or cycloalkene ring,
m represents 1, 2, 3 or 4, the substituents Z being selected independently when m is greater than 1, and
n represents 2 or 3.

Surprisingly, the substituted spiro-derivatives, according to the invention, of 3-(3,5-dihalogenophenyl)-oxazolidine-2,4-dione(thione-ones) exhibit a substantially higher fungicidal action, especially against species of Botrytis, than the compound tetramethyl-thiuram disulphide, known from the prior art, which is recognized as a good agent of the same type of action. The active compounds according to the invention thus represent an enrichment of the art.

Preferably, in formula (I), A represents oxygen or sulphur, X and Y are identical or different and each represent fluorine, chlorine, bromine or iodine, Z represents straight-chain or branched alkyl with 1 to 4 carbon atoms or a fused cyclopentane, cyclohexane, cyclopentene or cyclohexene ring, m represents 1, 2, 3, or 4, the substituents Z being selected independently when m is greater than 1, and n represents 2 or 3.

Very particularly preferred compounds of the formula (I) are those in which A represents oxygen, X and Y represent chlorine and n represents 2.

Specifically, the following compounds of the general formula (I) may be mentioned in addition to the compounds mentioned later in the preparative examples:

TABLE 1

| $Z_m$—(CH$_2$)$_n$ ring | A | X | Y |
|---|---|---|---|
| CH$_3$— (cyclopropyl) | S | Cl | Cl |
| C$_2$H$_5$— (cyclopropyl) | S | Cl | Cl |
| i-C$_3$H$_7$— (cyclopropyl) | S | Cl | Cl |
| t-C$_4$H$_9$— (cyclopropyl) | S | Cl | Cl |
| cyclobutyl | O | Cl | Cl |
| CH$_3$-cyclobutyl | O | Cl | Cl |
| CH$_3$,CH$_3$-cyclobutyl | O | Cl | Cl |
| CH$_3$,CH$_3$-cyclobutyl | O | Cl | Cl |
| CH$_3$,CH$_3$-cyclobutyl | O | Cl | Cl |

The invention also provides a process for the preparation of a spiro-derivative of a 3-(3,5-dihalogenophenyl)-oxazolidine-2,4-dione(thione-one) of the formula (I) in which an α-hydroxy-cycloalkylcarboxylic acid or an ester thereof of the general formula

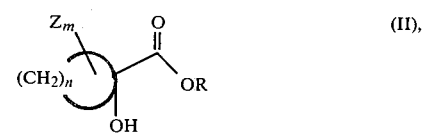

in which
R represents hydrogen or alkyl with 1 to 4 carbon atoms and
Z, m and n have the abovementioned meanings,
(a) is reacted with an isocyanate of the general formula

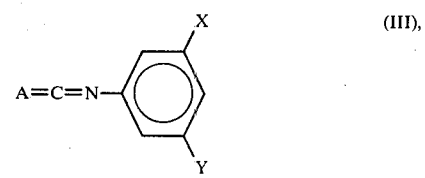

in which

A, X and Y have the abovementioned meanings, if appropriate in the presence of a base and in the presence of a diluent, or (b) is reacted with an aniline of the general formula

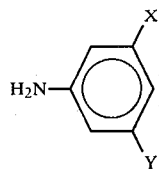
(IV), in which

X and Y have the abovementioned meanings, in the presence of a diluent, and the resulting α-hydroxycycloalkanecarboxylic acid amide of the general formula

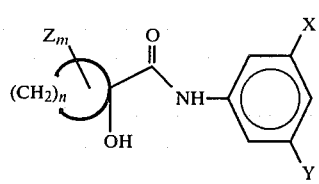
(V)

in which X, Y, Z, m and n have the abovementioned meanings, is cyclized with (thio)phosgene in the presence of a base.

If, for example, 1-hydroxy-2-methyl-cyclopropane-1-carboxylic acid and 3,5-dichlorophenyl isocyanate are used as starting materials in process variant (a), the course of the reaction can be represented by the following equation:

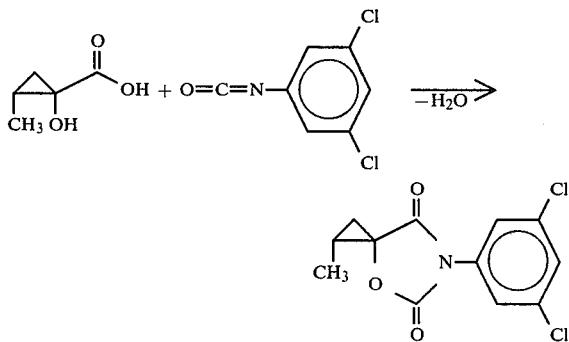

If, for example, 1-hydroxy-2-ethyl-cyclobutane-1-carboxylic acid ethyl ester and 3,5-dichlorophenyl isocyanate are used as starting materials in process variant (a), the course of the reaction can be represented by the following equation:

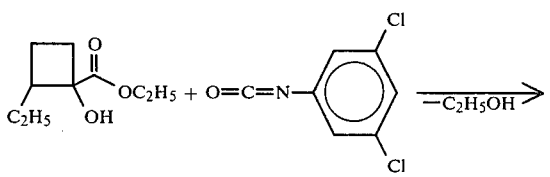

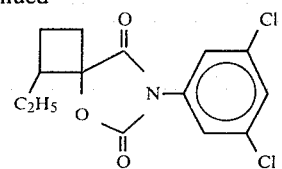

If, for example, 1-hydroxy-2-methyl-cyclopropane-1-carboxylic acid, 3,5-dichloroaniline and phosgene are used as starting materials in process variant (b) the course of the reaction can be represented by the following equation:

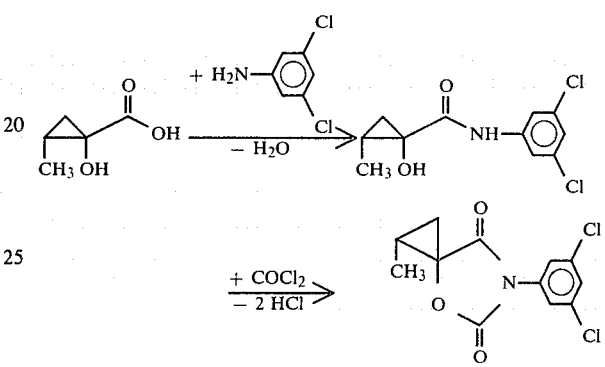

The formula (II) provides a general definition of the α-hydroxy-cycloalkyl-carboxylic acid (and esters) to be used as starting materials. In this formula, Z, m and n preferably have the meanings that have already been mentioned as preferred in connection with the description of the compounds of the formula (I). R preferably represents hydrogen, methyl or ethyl.

Starting compounds of the formula (II) are known (see, for example, Liebigs Ann. Chem. 1976, 463; J. Chem. Soc. 1938, 1211 and DE-OS (German Published Specification) No. 2,128,327). The following may be mentioned as examples: 1-hydroxy-2-methyl-cyclopropane-1-carboxylic acid and its methyl and ethyl esters; 1-hydroxy-2-ethylcyclopropane-1-carboxylic acid and its methyl and ethyl esters; 1-hydroxy-2-isopropyl-cyclopropane-1-carboxylic acid and its methyl and ethyl esters; 1-hydroxy-2-tert.-butyl-cyclopropane-1-carboxylic acid and its methyl and ethyl esters; 1-hydroxy-2,3-dimethyl-cyclopropane-1-carboxylic acid and its methyl and ethyl esters; 1-hydroxy-2,2,3,3-tetramethyl-cyclopropane-1-carboxylic acid and its methyl and ethyl esters and 1-hydroxy-3,3-dimethyl-cyclobutane-1-carboxylic acid and its methyl and ethyl esters.

The formula (III) provides a general definition of the isocyanates also to be used as starting materials, and the formula (IV) provides a general definition of the anilines. In these formulae, A, X and Y preferably have those meanings which have already been mentioned as preferred in connection with the description of the compounds of the formula (I).

The starting compounds of the formulae (III) and (IV) are generally known compounds of organic chemistry.

Preferred diluents for the reaction in accordance with process variant (a) are inert organic solvents. These include, as preferences, aromatic hydrocarbons (which may be halogenated), for example benzene, toluene, xylene or 1,2-dichlorobenzene, and aliphatic halogenated hydrocarbons, for example methylene chloride, chloroform or carbon tetrachloride.

If the reaction in accordance with process variant (a) is carried out in the presence of a base, any of the organic and inorganic bases usually employable can be utilized. These include, as preferences, tertiary amines, for example triethylamine or pyridine, and alcoholates, for example potassium tert.-butylate or sodium tert.-butylate.

In process variant (a), the reaction temperatures can be varied within a substantial range. In general, the reaction is carried out at from 20° to 150° C., preferably at the boiling point of the particular solvent.

In carrying out process variant (a), equimolar amounts of the reactants are preferably used. In general, if a base is used, it is employed in the equimolar amount if α-hydroxycycloalkanecarboxylic acids are used as starting materials, and only in catalytic amount if α-hydroxycycloalkanecarboxylic acid esters are employed. To isolate the compound of the formula (I), the solvent is distilled off and the residue is worked up in accordance with customary methods.

Preferred diluents for the reaction in accordance with process variant (b), are inert organic solvents. These include, as preferences, the solvents already mentioned in connection with process variant (a).

Preferred bases for the reaction in accordance with process variant (b) are the reagents already mentioned in connection with variant (a).

In process variant (b) the reaction temperatures can be varied within a substantial range. In general, the reaction is carried out at from 20° to 150° C., preferably at the boiling point of the solvent used.

In carrying out process variant (b) equimolar amounts of the reactants are preferably used. The α-hydroxy-cycloalkane-carboxylic acid amide of the formula (V) which is formed as an intermediate product can be reacted directly, without isolation. To isolate the compound of the formula (I), the solvent is distilled off and the residue is worked up in accordance with customary methods.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds at the concentrations required for combating plant diseases, permits treatment of above-ground parts of plants, of vegetative propagation stock and seeds, and of the soil.

As plant protection agents, the active compounds according to the invention can be used with particularly good success for combating Botrytis species, such as against the grey mould causative organism (*Botrytis cinerea*).

The active compounds can be converted into the customary formulations, such as solutions, emulsions, powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulfonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, from 1 to 0.0001% by weight, preferably from 0.5 to 0.001%.

In the treatment of seed, amounts of active compound of 0.001 to 50 g, especially 0.01 to 10 g, are generally employed per kilogram of seed.

For the treatment of soil, active compound concentrations of 0.00001 to 0.1% by weight, especially 0.0001 to 0.02%, are generally employed at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in following illustrative example:

EXAMPLE 1

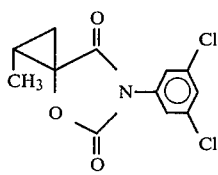

(1)

Process variant (a)

5.8 g (0.05 mol) of 1-hydroxy-2-methyl-cyclopropane-1-carboxylic acid and 5.05 g (0.05 mol) of triethylamine were dissolved in 200 ml of 1,2-dichlorobenzene at about 100° C. At this temperature, a solution of 9.4 g (0.05 mol) of 3,5-dichlorophenyl isocyanate in 50 ml of 1,2-dichlorobenzene was added dropwise, while stirring, and the mixture was then heated under reflux for 1 hour, under a water separator. After all the water had been separated off, the mixture was allowed to cool and was concentrated by distilling off the solvent in vacuo. 100 ml of hot ethanol were added to the residue while it was still warm, and the batch was mixed thoroughly.

During cooling, crystals separated out and these were filtered off, washed with a small amount of ethanol and dried. 7.2 g (50% of theory) of 1-oxa-3-aza-spiro-[4,2]-heptane-3-(3,5-dichlorophenyl)-6-methyl-2,4-dione of melting point 125°-27° C. were obtained.

The following compounds of the general formula

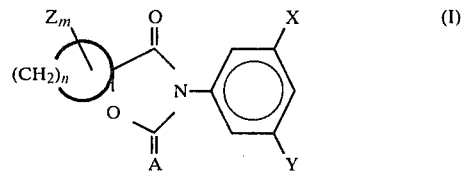

were obtained analogously, in accordance with process variant (a), or in accordance with process variant (b).

TABLE 2

| Compound No. | $Z_m$ $(CH_2)_n$ | A | X | Y | Melting point (°C.) |
|---|---|---|---|---|---|
| 2 | (cyclohexyl-spiro) | O | Cl | Cl | 172–75 |
| 3 | $CH_3$, $CH_3$, $CH_3$, $CH_3$ | O | Cl | Cl | 154 |
| 4 | i-$C_3H_7$ | O | Cl | Cl | 131 |
| 5 | $C_2H_5$ | O | Cl | Cl | 103 |
| 6 | t-$C_4H_9$ | O | Cl | Cl | 133–34 |

The fungicidal activity of the compounds of this invention is illustrated by the following example wherein the compound according to the present invention is identified by the number (given in brackets) from Example 1

EXAMPLE 2

Botrytis test (beans)/protective

Solvent: 4.7 parts by weight of acetone
Dispersing agent: 0.3 part by weight of alkylaryl polyglycol ether
Water: 95.0 parts by weight The amount of active compound required for the desired concentration of active compound in the spray liquor was mixed with the stated amount of the solvent and the concentrate was diluted with the stated amount of water which contained the stated amount of the dispersing agent.

Plants of Phaseolus vulgaris in the 2-leaf stage were sprayed with the spray liquor until dripping wet. After 24 hours, 2 small pieces of agar on which Botrytis cinerea had been grown were placed on each leaf. The inoculated plants were set up in a darkened, moist chamber at 20° C. 3 days after the inoculation, the size of the infection spots on the leaves was rated.

The ratings obtained were converted to percent infection. 0% meant no infection and 100% meant that the infection spot had developed completely.

In this test, for example, compound (1) showed a very good action which was superior to that of the compounds known from the prior art.

It will be appreciated that the instant specification and examples are set forth by way of illustration and not limitation, and that various modifications and changes may be made without departing from the spirit and scope of the present invention.

What is claimed is:

1. A substituted spiro-derivative of 3-(3,5-dihalogenophenyl)-oxazolidine-2,4-dione(thione-one) of the formula

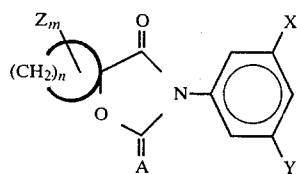

in which
A is oxygen or sulphur,
X and Y each independently is halogen,
Z each independently is alkyl with 1 to 4 carbon atoms or a fused cyclopentane, cyclohexane, cyclopentene or cyclohexene ring,
m is 1, 2, 3, or 4, and
n is 2 or 3.

2. A compound according to claim 1, in which said compound is

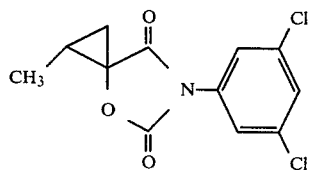

3. A compound according to claim 1, in which said compound is

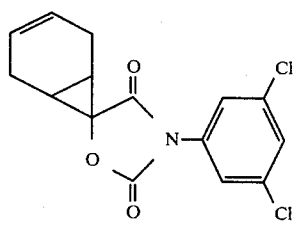

4. A compound according to claim 1, in which said compound is

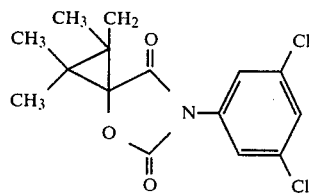

5. A compound according to claim 1, in which said compound is

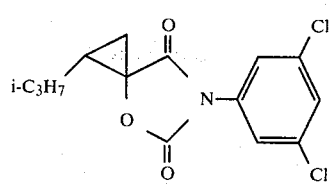

6. A compound according to claim 1, in which said compound is

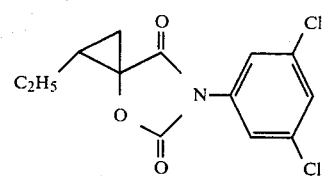

7. A compound according to claim 1, in which said compound is

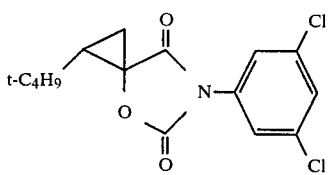

8. A fungicidal composition containing as active ingredient a fungicidally effective amount of a compound according to claim 1 in admixture with a diluent.

9. A method of combating fungi which comprises applying to the fungi, or to a habitat thereof, a fungicidally effective amount of a compound according to claim 1.

10. The method according to claim 9, in which said compound is

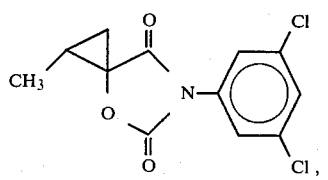

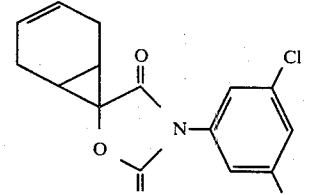

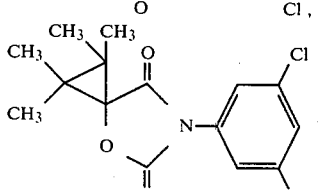

-continued
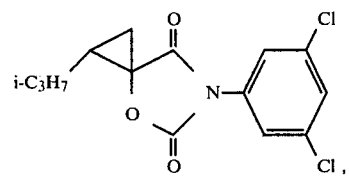
-continued
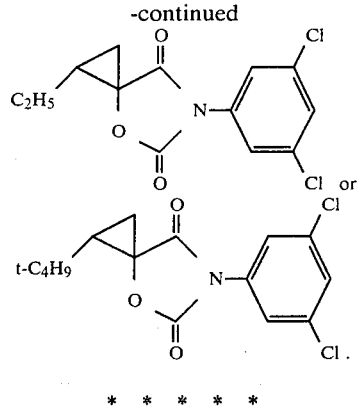
* * * * *

UNITED STATES PATENT AND TRADEMARK OFFICE
CERTIFICATE OF CORRECTION

PATENT NO. : 4,267,186

DATED : May 12, 1981

INVENTOR(S) : Hans-Joachim Knops et al

It is certified that error appears in the above-identified patent and that said Letters Patent are hereby corrected as shown below:

Column 9, line 61 Delete "  " and insert -- 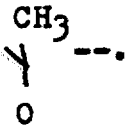 --.

Signed and Sealed this

Twentieth Day of October 1981

[SEAL]

Attest:

GERALD J. MOSSINGHOFF

Attesting Officer   Commissioner of Patents and Trademarks